US011471549B2

(12) United States Patent
Nakagawa et al.

(10) Patent No.: US 11,471,549 B2
(45) Date of Patent: Oct. 18, 2022

(54) STRETCHABLE FILM AND ARTICLE COMPRISING SAME

(71) Applicant: NITTO DENKO CORPORATION, Osaka (JP)

(72) Inventors: Muneshige Nakagawa, Ibaraki (JP); Kohei Takeda, Ibaraki (JP); Shinsuke Ikishima, Ibaraki (JP)

(73) Assignee: NITTO DENKO CORPORATION, Osaka (JP)

( * ) Notice: Subject to any disclaimer, the term of this patent is extended or adjusted under 35 U.S.C. 154(b) by 418 days.

(21) Appl. No.: 16/338,859

(22) PCT Filed: Sep. 14, 2017

(86) PCT No.: PCT/JP2017/033212
§ 371 (c)(1),
(2) Date: Apr. 2, 2019

(87) PCT Pub. No.: WO2018/066334
PCT Pub. Date: Apr. 12, 2018

(65) Prior Publication Data
US 2020/0197555 A1   Jun. 25, 2020

(30) Foreign Application Priority Data

Oct. 6, 2016 (JP) .............................. JP2016-197876
Mar. 27, 2017 (JP) .............................. JP2017-060835

(51) Int. Cl.
*A61L 9/014* (2006.01)
*B32B 7/02* (2019.01)
(Continued)

(52) U.S. Cl.
CPC .......... *A61L 9/014* (2013.01); *A41D 13/1192* (2013.01); *A61F 13/51* (2013.01);
(Continued)

(58) Field of Classification Search
CPC . A61L 9/014; A61L 2209/22; A41D 13/1192; B01J 20/06; B01J 20/043;
(Continued)

(56) References Cited

U.S. PATENT DOCUMENTS 5,110,586 A * 5/1992 Kurihara ................. C01G 9/02
106/426
5,185,035 A   2/1993 Brown et al.
(Continued)

FOREIGN PATENT DOCUMENTS

CN  202637282 U  1/2013
CN  203152561 U  8/2013
(Continued)

OTHER PUBLICATIONS

Russian Office Action dated Jul. 29, 2020, issued in corresponding Russian patent application No. 2019110132 with English machine translation thereof.
(Continued)

*Primary Examiner* — Catherine A. Simone
(74) *Attorney, Agent, or Firm* — Greenblum & Bernstein, P.L.C.

(57) ABSTRACT

Provided is a stretchable film having excellent stretchability, excellent air permeability, and an excellent deodorizing property. Also provided is an article including such stretchable film. A stretchable film of the present invention is a film having stretchability, and includes a deodorant. The stretchable film of the present invention is a film having stretchability, and has a deodorization efficiency for each of ammonia and hydrogen sulfide 3 hours after the start of a deodorization test, the deodorization efficiency being measured by a detector tube method, of 10% or more.

27 Claims, 8 Drawing Sheets

(51) Int. Cl.
*B32B 27/08* (2006.01)
*B32B 27/20* (2006.01)
*B32B 27/32* (2006.01)
*A41D 13/11* (2006.01)
*A61F 13/51* (2006.01)
*B01J 20/04* (2006.01)
*B01J 20/06* (2006.01)
*B01J 20/10* (2006.01)
*B01J 20/26* (2006.01)
*B01J 20/28* (2006.01)
*A61F 13/514* (2006.01)

(52) U.S. Cl.
CPC ............ *B01J 20/043* (2013.01); *B01J 20/06* (2013.01); *B01J 20/103* (2013.01); *B01J 20/261* (2013.01); *B01J 20/28035* (2013.01); *B32B 7/02* (2013.01); *B32B 27/08* (2013.01); *B32B 27/20* (2013.01); *B32B 27/32* (2013.01); *A61F 2013/5109* (2013.01); *A61F 2013/51429* (2013.01); *A61L 2209/22* (2013.01); *B32B 2250/03* (2013.01); *B32B 2250/242* (2013.01); *B32B 2250/40* (2013.01); *B32B 2264/104* (2013.01); *B32B 2555/02* (2013.01); *Y10T 428/2495* (2015.01)

(58) Field of Classification Search
CPC .. B01J 20/103; B01J 20/261; B01J 20/28035; B01J 20/10; B32B 7/02; B32B 27/08; B32B 27/20; B32B 27/32; B32B 2250/03; B32B 2250/242; B32B 2250/40; B32B 2264/104; B32B 2555/02; A61F 2013/5109; A61F 2013/51429; Y10T 428/258
See application file for complete search history.

(56) References Cited

U.S. PATENT DOCUMENTS

| | | | |
|---|---|---|---|
| 5,501,679 A | 3/1996 | Krueger et al. | |
| 5,691,034 A | 11/1997 | Krueger et al. | |
| 5,713,884 A * | 2/1998 | Osborn, III | A61F 13/51466 604/385.24 |
| 5,891,508 A | 4/1999 | Barnum | |
| 10,371,677 B2 | 8/2019 | Nakada et al. | |
| 2005/0208294 A1 * | 9/2005 | Kaufman | A61L 15/62 428/330 |
| 2006/0189738 A1 * | 8/2006 | Ueda | A61L 15/60 524/413 |
| 2008/0011632 A1 | 1/2008 | Albino | |
| 2008/0076315 A1 | 3/2008 | McCormack et al. | |
| 2010/0211034 A1 * | 8/2010 | Fish et al. | |
| 2015/0037906 A1 | 2/2015 | Nakada et al. | |
| 2016/0370331 A1 | 12/2016 | Nakada et al. | |

FOREIGN PATENT DOCUMENTS

| | | |
|---|---|---|
| CN | 104136920 A | 11/2014 |
| CN | 104524625 A | 4/2015 |
| EP | 2806269 | 11/2014 |
| JP | 63-229142 | 9/1988 |
| JP | 5-501386 | 3/1993 |
| JP | 2000-117911 A | 4/2000 |
| JP | 2001-218791 | 8/2001 |
| JP | 2006-028453 | 2/2006 |
| JP | 2007-159632 | 6/2007 |
| JP | 2012-035256 | 2/2012 |
| JP | 2014-059217 | 4/2014 |
| JP | 2015/034366 | 2/2015 |
| JP | 2016-069501 | 5/2016 |
| RU | 2345745 C2 | 2/2009 |

OTHER PUBLICATIONS

Chinese Office Action dated Jun. 3, 2020, issued in corresponding Chinese patent application No. 201780061318.2 with English machine translation thereof.

Dingyi Hong, Handbook of Plastic Industry Polyolefin, Chemical Industry Press, Dec. 31, 1998, p. 624 with English translation thereof.

Extended European Search Report dated Mar. 26, 2020 in European Application No. 17858173.2.

International Search Report in International Patent Application No. PCT/JP2017/033212, dated Dec. 5, 2017.

* cited by examiner

STRETCHABLE FILM AND ARTICLE COMPRISING SAME

TECHNICAL FIELD

The present invention relates to a stretchable film and an article including the stretchable film.

BACKGROUND ART

Various stretchable films are adopted for articles including sanitary articles, such as a diaper and a mask (Patent Literature 1).

Such stretchable film is required to have not only excellent stretchability but also excellent air permeability in view of applications such as a diaper and a mask.

Meanwhile, many of the articles including sanitary articles, such as a diaper and a mask, are each required to have deodorizing performance.

An article for absorbing a body fluid using a back sheet having air permeability and a deodorizing effect has been reported as related art related to a sanitary article having imparted thereto deodorizing performance (Patent Literature 2). However, the article for absorbing a body fluid is intended only to achieve both the air permeability and the deodorizing effect, and involves a problem in that the article may not express stretchability. In addition, the article involves a problem in that each of the air permeability and the deodorizing effect is still at a level unsuitable for practical use.

An air-permeable porous sheet that may suppress the passage of an odor while sufficiently securing air permeability has been reported as another related art related to a sanitary article having imparted thereto deodorizing performance (Patent Literature 3). However, the air-permeable porous sheet is intended only to achieve both the air permeability and the suppression of the passage of the odor, and involves a problem in that the sheet may not express stretchability. In addition, the sheet involves a problem in that each of its air permeability and deodorizing effect is still at a level unsuitable for practical use. Further, the suppression of the passage of the odor is performed by physical adsorption to the inside of each of porous zeolite particles, and hence the sheet involves a problem in that even an aroma needed for a sanitary article or the like is adsorbed, and a problem in that an odor that has adsorbed to the sheet once is emitted by changes in temperature and humidity to return to an environment where the odor is originally present.

CITATION LIST

Patent Literature

[PTL 1] JP 05-501386 A
[PTL 2] JP 2001-218791 A
[PTL 3] JP 2007-159632 A

SUMMARY OF INVENTION

Technical Problem

The present invention has been made to solve the conventional problems, and an object of the present invention is to provide a stretchable film having excellent stretchability, excellent air permeability, and an excellent deodorizing property. Another object of the present invention is to provide an article including such stretchable film.

Solution to Problem

A stretchable film according to one embodiment of the present invention is a film having stretchability, and includes a deodorant.

In one embodiment, the deodorant includes a chemical adsorption deodorant.

In one embodiment, the chemical adsorption deodorant contains silicon dioxide and zinc oxide.

In one embodiment, a total content of silicon dioxide and zinc oxide in the chemical adsorption deodorant is from 50 wt % to 100 wt %.

In one embodiment, a content ratio between silicon dioxide and zinc oxide in the chemical adsorption deodorant is from 5:95 to 95:5 in terms of weight ratio.

In one embodiment, a content ratio between silicon dioxide and zinc oxide in the chemical adsorption deodorant is from 60:40 to 80:20 in terms of weight ratio.

In one embodiment, the stretchable film according to the embodiment of the present invention includes: an olefin-based resin; and a filler.

In one embodiment, the olefin-based resin contains an olefin-based elastomer.

In one embodiment, the olefin-based elastomer contains an α-olefin-based elastomer.

In one embodiment, the α-olefin-based elastomer includes a propylene-based elastomer.

In one embodiment, the filler includes at least one kind selected from inorganic particles and organic particles.

In one embodiment, the filler includes inorganic particles.

In one embodiment, the inorganic particles include at least one kind selected from talc, titanium oxide, calcium oxide, magnesium oxide, zinc oxide, titanium oxide, calcium carbonate, silica, clay, mica, barium sulfate, whisker, and magnesium hydroxide.

In one embodiment, the inorganic particles include calcium carbonate.

In one embodiment, the stretchable film according to the embodiment of the present invention is obtained by subjecting an unstretched film to a stretching treatment.

In one embodiment, the stretchable film according to the embodiment of the present invention is formed of a laminate of two or more layers, and the deodorant is incorporated into at least one layer of the layers forming the laminate.

In one embodiment, the deodorant is incorporated into at least one layer of outer layers.

In one embodiment, the stretchable film according to the embodiment of the present invention is formed of a laminate of three layers.

In one embodiment, when a layer construction of the laminate is represented by A layer, B layer, and C layer in the stated order, the deodorant is incorporated into the A layer only; the B layer only; the C layer only; both of the A layer and the B layer; both of the B layer and the C layer; both of the A layer and the C layer; and all of the A layer, the B layer, and the C layer.

In one embodiment, the deodorant is incorporated into all of the A layer, the B layer, and the C layer.

In one embodiment, the stretchable film according to the embodiment of the present invention is formed of a laminate of three layers, and when a layer construction of the laminate is represented by A layer, B layer, and C layer in the stated order, the A layer and the C layer serving as surface layers each have a thickness of from 2 μm to 40 μm.

In one embodiment, the stretchable film according to the embodiment of the present invention is formed of a laminate of three layers, and when a layer construction of the laminate is represented by A layer, B layer, and C layer in the stated order, the B layer serving as an intermediate layer has a thickness of from 10 μm to 70 μm.

In one embodiment, the deodorant includes a chemical adsorption deodorant.

In one embodiment, the chemical adsorption deodorant contains silicon dioxide and zinc oxide.

In one embodiment, a total content of silicon dioxide and zinc oxide in the chemical adsorption deodorant is from 50 wt % to 100 wt %.

In one embodiment, a content ratio between silicon dioxide and zinc oxide in the chemical adsorption deodorant is from 5:95 to 95:5 in terms of weight ratio.

In one embodiment, a content ratio between silicon dioxide and zinc oxide in the chemical adsorption deodorant is from 60:40 to 80:20 in terms of weight ratio.

In one embodiment, the stretchable film according to the embodiment of the present invention has a deodorization efficiency for each of ammonia and hydrogen sulfide 3 hours after a start of a deodorization test, the deodorization efficiency being measured by a detector tube method, of 10% or more, provided that the deodorization efficiency is calculated as described in the following measurement method (i) or (ii):

Measurement method (i): The stretchable film serving as a measurement object, which has been cut into a size measuring 140 mm by 200 mm, is loaded into a Tedlar bag having a volume of 3 L in a thermohygrostatic chamber at 20° C. and 65% RH; next, 3 L of odorless air that has been passed through activated carbon is sealed in the Tedlar bag, and then an odor gas is injected into the Tedlar bag so that a predetermined initial gas concentration P is obtained (an initial gas concentration of 100 ppm is obtained for ammonia, and an initial gas concentration of 4 ppm is obtained for hydrogen sulfide); after that, a gas concentration is monitored with a gas detector tube (manufactured by Gastec Corporation) with time, and a gas concentration Q 3 hours after a start of the monitoring is measured; $[(P-Q)/P] \times 300 = X$ (%) is calculated, and the X (%) is defined as a gas concentration reduction ratio; meanwhile, the stretchable film serving as a measurement object is subjected to the same measurement without being loaded into the Tedlar bag, and a gas concentration $Q_0$ 3 hours after a start of the measurement is measured; $[(P-Q_0)/P] \times 100 = Y$ (%) is calculated, and the Y (%) is defined as a blank gas concentration reduction ratio; and (X−Y) (%) is calculated from the gas concentration reduction ratio X (%) and the blank gas concentration reduction ratio Y (%) thus obtained, and is defined as the deodorization efficiency;

Measurement method (ii): The stretchable film serving as a measurement object, which has been cut into a size measuring 100 mm by 100 mm, is loaded into Smart Bag PA having a volume of 5 L (manufactured by GL Sciences Inc.) in a thermohygrostatic chamber at 25° C. and 20% RH; next, 2 L of odorless air that has been passed through activated carbon is sealed in the Smart Bag PA, and then an odor gas is injected into the Smart Bag PA so that a predetermined initial gas concentration P is obtained (an initial gas concentration of 100 ppm is obtained for ammonia, and an initial gas concentration of 4 ppm is obtained for hydrogen sulfide); after that, a gas concentration is monitored with a gas detector tube (manufactured by Gastec Corporation) with time, and a gas concentration Q 3 hours after a start of the monitoring is measured; $[(P-Q)/P] \times 100 = X$ (%) is calculated, and the X (%) is defined as a gas concentration reduction ratio; meanwhile, the stretchable film serving as a measurement object is subjected to the same measurement without being loaded into the Smart Bag PA, and a gas concentration $Q_0$ 3 hours after a start of the measurement is measured; $[(P-Q_0)/P] \times 100 = Y$ (%) is calculated, and the Y (%) is defined as a blank gas concentration reduction ratio; and (X−Y) (%) is calculated from the gas concentration reduction ratio X (%) and the blank gas concentration reduction ratio Y (%) thus obtained, and is defined as the deodorization efficiency.

In one embodiment, the stretchable film according to the embodiment of the present invention has an air permeability measured with an Oken-type air permeability meter of less than 99, 999 sec/100 cc.

In one embodiment, the stretchable film according to the embodiment of the present invention has an extension direction in which an air permeability measured with an Oken-type air permeability meter under a state in which the film is extended by 100% becomes less than 60,000 sec/100 cc.

In one embodiment, the stretchable film according to the embodiment of the present invention has a tensile direction in which a residual strain in the following case becomes 10 mm or less: in a hysteresis test, a test piece of the film having a width of 20 mm is pulled from a chuck-to-chuck distance of 30 mm to a chuck-to-chuck distance of 60 mm at a tensile rate of 50 mm/min and held for 1 minute, and then the tension of the chuck-to-chuck distance is removed.

In one embodiment, the stretchable film according to the embodiment of the present invention is used in a sanitary article.

An article according to one embodiment of the present invention includes the stretchable film according to the embodiment of the present invention.

Advantageous Effects of Invention

According to the present invention, the stretchable film having excellent stretchability, excellent air permeability, and an excellent deodorizing property may be provided. The article including such stretchable film may also be provided.

DESCRIPTION OF EMBODIMENTS

<<Stretchable Film>>

Figure 1:
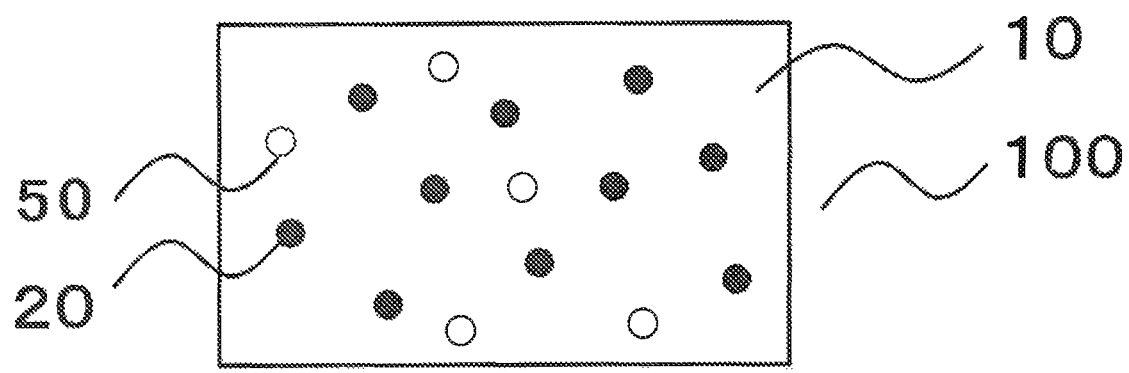
FIG. 1 is a schematic plan view of an example of a stretchable film according to one embodiment of the present invention.

A stretchable film of the present invention is a film having stretchability. The stretchable film of the present invention has stretchability, and hence has excellent air permeability.

The stretchable film according to one embodiment of the present invention includes a deodorant. The stretchable film of the present invention includes the deodorant, and hence may express excellent stretchability, excellent air permeability, and an excellent deodorizing property.

Examples of the deodorant include: a chemical adsorption deodorant that expresses its deodorizing effect through chemical adsorption; a physical adsorption deodorant that expresses its deodorizing effect through physical adsorption (e.g., activated carbon, bamboo charcoal, or zeolite); a biological deodorant that expresses its deodorizing effect through a biological action (e.g., a microbicide or an antimicrobial agent); a masking deodorant that expresses its deodorizing effect through a masking action (e.g., a perfume); and a photocatalyst deodorant that expresses its deodorizing effect through a photocatalytic action (e.g., titanium oxide).

In consideration of the fact that the stretchable film of the present invention is suitably used in a sanitary article or the like, in the present invention, the chemical adsorption deodorant is preferably selected as the deodorant. When the physical adsorption deodorant is selected, even an aroma needed for a sanitary article or the like may be adsorbed, or an odor that has adsorbed to the deodorant once may be emitted by changes in temperature and humidity to return to an environment where the odor is originally present (to cause odor return). When the biological deodorant is selected, it may be difficult to sufficiently remove an odor that has volatilized into air. When the masking deodorant is selected, an odor that is to be removed and the odor of masking may be mixed with each other to produce an unpleasant odor, and the persistence of the deodorizing effect may be poor. When the photocatalyst deodorant is selected, the deodorizing effect may not be expressed unless light sufficiently strikes the deodorant. Meanwhile, the chemical adsorption deodorant has a high deodorization rate, has persistence, hardly removes an aroma needed for a sanitary article or the like, hardly causes odor return observed in the physical adsorption deodorant or the like, may sufficiently remove even an odor that has volatilized into air, is free from producing an unpleasant odor due to the mixing of odors resulting from the masking action, and may express its deodorizing effect even when no light strikes the deodorant.

Examples of the chemical adsorption deodorant include various metal oxides. It has been found that particularly when the combination of silicon dioxide and zinc oxide out of those metal oxides is adopted, the effects of the present invention may be expressed to a larger extent. That is, in the present invention, the deodorant is preferably a chemical adsorption deodorant, and the chemical adsorption deodorant more preferably contains silicon dioxide and zinc oxide. It has been found that when a chemical adsorption deodorant containing silicon dioxide and zinc oxide is adopted as the deodorant in the present invention, the deodorant may express deodorizing effects on both of a basic odor and an acidic odor, and it has been found that the deodorant may typically express deodorizing effects on, for example, both of amine-based odors, such as an ammonia odor, and sulfur-based odors, such as a hydrogen sulfide odor. The amine-based odors, such as the ammonia odor, and the sulfur-based odors, such as the hydrogen sulfide odor, are known as the four worst odors (ammonia, triethylamine, hydrogen sulfide, and methyl mercaptan odors), and hence an ability to remove any such bad odor is an indicator representing an extremely excellent deodorizing effect.

When the deodorant is a chemical adsorption deodorant containing silicon dioxide and zinc oxide, the total content of silicon dioxide and zinc oxide in the chemical adsorption deodorant is preferably from 50 wt % to 100 wt %, more preferably from 70 wt % to 100 wt %, still more preferably from 90 wt % to 100 wt %, particularly preferably from 95 wt % to 100 wt %, most preferably substantially 100 wt %. When the total content of silicon dioxide and zinc oxide in the chemical adsorption deodorant falls within the range, the stretchable film of the present invention may express an extremely excellent deodorizing property while maintaining excellent stretchability and excellent air permeability.

When the deodorant is a chemical adsorption deodorant containing silicon dioxide and zinc oxide, a content ratio between silicon dioxide and zinc oxide in the chemical adsorption deodorant is preferably from 5:95 to 95:5 in terms of weight ratio, more preferably from 15:85 to 90:10, still more preferably from 30:70 to 90:10, particularly preferably from 50:50 to 85:15, most preferably from 60:40 to 80:20. When the content ratio between silicon dioxide and zinc oxide in the chemical adsorption deodorant falls within the range, the stretchable film of the present invention may express an extremely excellent deodorizing property while maintaining excellent stretchability and excellent air permeability.

In the case where the stretchable film of the present invention is formed only of one layer, the content of the deodorant in the stretchable film of the present invention is preferably from 0.005 wt % to 2.0 wt %, more preferably from 0.01 wt % to 1.6 wt %, still more preferably from 0.01 wt % to 1.3 wt %, still furthermore preferably from 0.02 wt % to 1.0 wt % with respect to the total weight (100 wt %) of the stretchable film. In the case where the stretchable film of the present invention is formed only of one layer, when the content of the deodorant in the stretchable film of the present invention falls within the range, the stretchable film of the present invention may express a more excellent deodorizing property while maintaining excellent stretchability and excellent air permeability. In the case where the stretchable film of the present invention is formed only of one layer, when the content of the deodorant in the stretchable film of the present invention deviates from the range to be excessively low, the stretchable film of the present invention may be unable to express an excellent deodorizing property. In the case where the stretchable film of the present invention is formed only of one layer, when the content of the deodorant in the stretchable film of the present invention deviates from the range to be excessively high, the stretchable film of the present invention may be unable to maintain excellent stretchability and excellent air permeability.

When the stretchable film of the present invention is formed of a laminate of two or more layers, the deodorant only needs to be incorporated into at least one layer of the layers forming the laminate. The deodorant is preferably incorporated into at least one layer of the outer layers of the film in order that the stretchable film of the present invention may express a more excellent deodorizing property.

When the stretchable film of the present invention is formed of a laminate of two layers (A layer and B layer), the deodorant may be incorporated only into the A layer, may be incorporated into the B layer only, or may be incorporated into both of the A layer and the B layer.

When the stretchable film of the present invention is formed of a laminate of three layers (A layer, B layer, and C layer in the stated order), the deodorant may be incorporated only into the A layer, may be incorporated only into the B layer, may be incorporated only into the C layer, may be incorporated only into both of the A layer and the B layer, may be incorporated only into both of the B layer and the C layer, may be incorporated only into both of the A layer and the C layer, or may be incorporated into all of the A layer, the B layer, and the C layer.

Also when the stretchable film of the present invention is formed of a laminate of four or more layers, the deodorant only needs to be incorporated in the same pattern as that described above.

In the case where the stretchable film of the present invention is formed of a laminate of two or more layers, the content of the deodorant in at least one layer of the outer layers, into which the deodorant is incorporated, is preferably from 0.001 wt % to 20 wt %, more preferably from 0.01 wt % to 15 wt %, still more preferably from 0.05 wt % to 10 wt %, particularly preferably from 0.1 wt % to 2 wt % with respect to the total weight (100 wt %) of the layer. In the case where the stretchable film of the present invention is formed of a laminate of two or more layers, when the content of the deodorant in at least one layer of the outer layers, into which the deodorant is incorporated, falls within the range, the stretchable film of the present invention may express a more excellent deodorizing property while maintaining excellent stretchability and excellent air permeability. In the case where the stretchable film of the present invention is formed of a laminate of two or more layers, when the content of the deodorant in at least one layer of the outer layers, into which the deodorant is incorporated, deviates from the range to be excessively low, the stretchable film of the present invention may be unable to express an excellent deodorizing property. In the case where the stretchable film of the present invention is formed of a laminate of two or more layers, when the content of the deodorant in at least one layer of the outer layers, into which the deodorant is incorporated, deviates from the range to be excessively high, the stretchable film of the present invention may be unable to maintain excellent stretchability and excellent air permeability.

The stretchable film according to one embodiment of the present invention has a deodorization efficiency for each of ammonia and hydrogen sulfide 3 hours after the start of a deodorization test, the deodorization efficiency being measured by a detector tube method, of 10% or more. The deodorization efficiency is preferably 10% or more, more preferably 20% or more, still more preferably 40% or more, particularly preferably 60% or more. The upper limit value of the deodorization efficiency is theoretically 100%. When the deodorization efficiency falls within the range, the stretchable film of the present invention may express deodorizing effects on both of amine-based odors, such as an ammonia odor, and sulfur-based odors, such as a hydrogen sulfide odor. That is, the stretchable film of the present invention may remove bad odors known as the four worst odors (ammonia, triethylamine, hydrogen sulfide, and methyl mercaptan odors), and hence shows an extremely excellent deodorizing effect.

The deodorization efficiency is calculated as described in the following measurement method (i) or (ii).

Measurement method (i): The stretchable film serving as a measurement object, which has been cut into a size measuring 140 mm by 200 mm, is loaded into a Tedlar bag having a volume of 3 L in a thermohygrostatic chamber at 20° C. and 65% RH. Next, 3 L of odorless air that has been passed through activated carbon is sealed in the Tedlar bag, and then an odor gas is injected into the Tedlar bag so that a predetermined initial gas concentration P may be obtained (an initial gas concentration of 100 ppm may be obtained for ammonia, and an initial gas concentration of 4 ppm may be obtained for hydrogen sulfide). After that, a gas concentration is monitored with a gas detector tube (manufactured by Gastec Corporation) with time, and a gas concentration Q 3 hours after the start of the monitoring is measured. $[(P-Q)/P] \times 100 = X$ (%) is calculated, and the X (%) is defined as a gas concentration reduction ratio. Meanwhile, the stretchable film serving as a measurement object is subjected to the same measurement without being loaded into the Tedlar bag, and a gas concentration $Q_0$ 3 hours after the start of the measurement is measured. $[(P-Q_0)/P] \times 100 = Y$ (%) is calculated, and the Y (%) is defined as a blank gas concentration reduction ratio. (X−Y) (%) is calculated from the gas concentration reduction ratio X (%) and the blank gas concentration reduction ratio Y (%) thus obtained, and is defined as the deodorization efficiency.

Measurement method (ii): The stretchable film serving as a measurement object, which has been cut into a size measuring 100 mm by 100 mm, is loaded into Smart Bag PA having a volume of 5 L (manufactured by GL Sciences Inc.) in a thermohygrostatic chamber at 25° C. and 20% RH. Next, 2 L of odorless air that has been passed through activated carbon is sealed in the Smart Bag PA, and then an odor gas is injected into the Smart Bag PA so that a predetermined initial gas concentration P may be obtained (an initial gas concentration of 100 ppm may be obtained for ammonia, and an initial gas concentration of 4 ppm may be obtained for hydrogen sulfide). After that, a gas concentration is monitored with a gas detector tube (manufactured by Gastec Corporation) with time, and a gas concentration Q 3 hours after the start of the monitoring is measured. $[(P-Q)/P] \times 100 = X$ (%) is calculated, and the X (%) is defined as a gas concentration reduction ratio. Meanwhile, the stretchable film serving as a measurement object is subjected to the same measurement without being loaded into the Smart Bag PA, and a gas concentration $Q_0$ 3 hours after the start of the measurement is measured. $[(P-Q_0)/P] \times 100 = Y$ (%) is calculated, and the Y (%) is defined as a blank gas concentration reduction ratio. (X−Y) (%) is calculated from the gas concentration reduction ratio X (%) and the blank gas concentration reduction ratio Y (%) thus obtained, and is defined as the deodorization efficiency.

The air permeability of the stretchable film of the present invention measured with an Oken-type air permeability meter is preferably less than 99,999 sec/100 cc, more preferably less than 80,000 sec/100 cc, still more preferably less than 70,000 sec/100 cc, still further more preferably less than 60,000 sec/100 cc, particularly preferably less than 50,000 sec/100 cc, most preferably less than 40,000 sec/100 cc. When the air permeability of the stretchable film of the present invention measured with the Oken-type air permeability meter falls within the range, the stretchable film of the present invention may have more excellent air permeability.

The stretchable film of the present invention preferably has an extension direction in which an air permeability measured with an Oken-type air permeability meter under a state in which the film is extended by 100% becomes less than 60,000 sec/100 cc. The air permeability is more preferably less than 50,000 sec/100 cc, still more preferably less than 40,000 sec/100 cc, still further more preferably less than 30,000 sec/100 cc, particularly preferably less than 10,000 sec/100 cc, most preferably less than 5,000 sec/100 cc. When the stretchable film of the present invention has an extension direction in which the air permeability measured with the Oken-type air permeability meter under a state in which the film is extended by 100% falls within the range, the stretchable film of the present invention may have excellent air permeability under an extended state.

The phrase "has an extension direction" means that the stretchable film of the present invention only needs to have at least one extension direction in which the above-mentioned air permeability falls within the above-mentioned range. Typically, when the stretchable film of the present invention is an unstretched film, such extension direction is preferably, for example, any one of all the directions of the film, and when the stretchable film of the present invention is a uniaxially stretched film, the direction is preferably, for example, a direction perpendicular to the direction of the stretching (a CD direction when the film is stretched in a machine (MD) direction). In addition, when the stretchable film of the present invention is a biaxially stretched film, an extension direction in which the above-mentioned air permeability falls within the above-mentioned range depends on various conditions, such as whether the stretching is simultaneous stretching or sequential stretching, and a difference in stretching ratio between the two axes.

The stretchable film of the present invention preferably has a tensile direction in which a residual strain in the following case becomes 10 mm or less: in a hysteresis test, a test piece of the film having a width of 20 mm is pulled from a chuck-to-chuck distance of 30 mm to a chuck-to-chuck distance of 60 mm at a tensile rate of 50 mm/min and held for 1 minute, and then the tension of the chuck-to-chuck distance is removed. The residual strain is more preferably from 9 mm to 1 mm, still more preferably from 8 mm to 1 mm, still further more preferably from 7 mm to 1 mm, particularly preferably from 6 man to 2 mm, most preferably from 5 mm to 3 mm. When the stretchable film of the present invention has a tensile direction in which the residual strain falls within the range, the stretchable film of the present invention may have more excellent stretchability.

The phrase "has a tensile direction" means that the stretchable film of the present invention only needs to have at least one tensile direction in which the above-mentioned residual strain falls within the above-mentioned range. Typically, when the stretchable film of the present invention is an unstretched film, such tensile direction is preferably, for example, any one of all the directions of the film, and when the stretchable film of the present invention is a uniaxially stretched film, the direction is preferably, for example, a direction perpendicular to the direction of the stretching (the CD direction when the film is stretched in the machine (MD) direction). In addition, when the stretchable film of the present invention is a biaxially stretched film, a tensile direction in which the above-mentioned residual strain falls within the above-mentioned range depends on various conditions, such as whether the stretching is simultaneous stretching or sequential stretching, and a difference in stretching ratio between the two axes.

The thickness of the stretchable film of the present invention is preferably from 30 μm to 300 μm, more preferably from 40 μm to 200 μm, still more preferably from 50 μm to 150 μm, particularly preferably from 60 μm to 140 μm, most preferably from 70 μm to 120 μm. When the thickness of the stretchable film of the present invention falls within the range, the stretchable film of the present invention may express more excellent stretchability, more excellent air permeability, and a more excellent deodorizing property.

The stretchable film of the present invention preferably further includes an olefin-based resin and a filler.

The stretchable film of the present invention may be formed only of one layer, or may be formed of a laminate of two or more layers.

FIG. 1 is a schematic plan view of an example of a stretchable film according to one embodiment of the present invention. In FIG. 1, a stretchable film 100 includes an olefin-based resin 10, a filler 20, and a deodorant 50.

Figure 2:
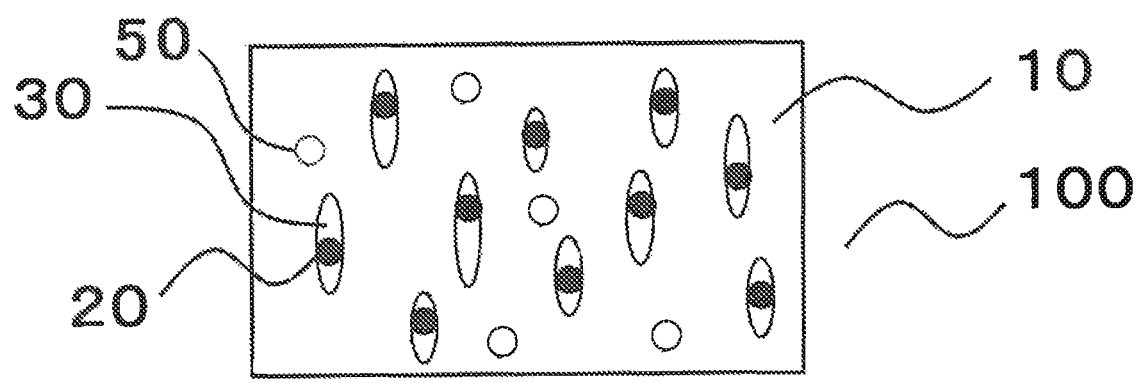
FIG. 2 is a schematic plan view of an example of the stretchable film according to another embodiment of the present invention.

FIG. 2 is a schematic plan view of an example of the stretchable film according to another embodiment of the present invention. In FIG. 2, the stretchable film 100 includes the olefin-based resin 10, the filler 20, and the deodorant 50, and further includes voids 30.

When the stretchable film of the present invention is such embodiment as illustrated in FIG. 1, the stretchable film may be turned into such embodiment as illustrated in FIG. 2 by being stretched. That is, when the stretchable film of the present invention is such embodiment as illustrated in FIG. 1, the stretching of the stretchable film of the present invention may produce appropriate voids in its surface. The stretchable film of the present invention may express sufficient air permeability because of the appropriate voids.

In the case where the stretchable film of the present invention is such embodiment as illustrated in FIG. 1, the stretchable film may express excellent air permeability even when not stretched. In addition, in the case where the stretchable film of the present invention is such embodiment as illustrated in FIG. 1, the stretchable film may express more excellent air permeability by being stretched.

In the case where the stretchable film of the present invention is such embodiment as illustrated in FIG. 2, the stretchable film may express excellent air permeability even when not stretched. In addition, in the case where the stretchable film of the present invention is such embodiment as illustrated in FIG. 2, the stretchable film may express more excellent air permeability by being stretched.

Such embodiment as illustrated in FIG. 1 or such embodiment as illustrated in FIG. 2 may be adopted as the stretchable film of the present invention in accordance with performance required of a site to be used in applications of, for example, sanitary articles, such as a diaper or a mask. For example, when the stretchable film of the present invention is such embodiment as illustrated in FIG. 1, the embodiment being capable of expressing excellent air permeability even when not stretched, the stretchable film may be preferably used in a site where expansion and contraction hardly occur, the site being required to have air permeability. In addition, for example, when the stretchable film of the present invention is such embodiment as illustrated in FIG. 1, the embodiment being capable of expressing excellent air permeability by being stretched, the stretchable film may be preferably used in a site where expansion and contraction occur, the site being required to have air permeability. Further, when the stretchable film of the present invention is such embodiment as illustrated in FIG. 2, the stretchable film may be preferably used in a site where expansion and contraction hardly occur, the site being required to have air permeability, or in a site where expansion and contraction occur, the site being required to have air permeability.

Figure 3:
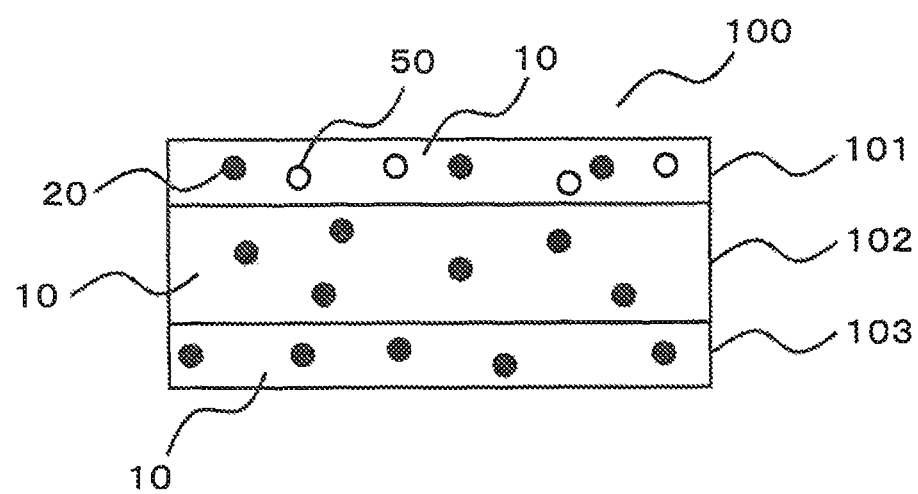
FIG. 3 is a schematic sectional view of an example of the stretchable film according to another embodiment of the present invention.

FIG. 3 is a schematic sectional view of an example of the stretchable film according to another embodiment of the present invention. In FIG. 3, the stretchable film 100 is formed of a laminate of three layers (A layer 101, B layer 102, and C layer 103), the A layer 101 contains the olefin-based resin 10, the filler 20, and the deodorant 50, the B layer 102 contains the olefin-based resin 10 and the filler 20, and is free of the deodorant 50, and the C layer 103 contains the olefin-based resin 10 and the filler 20, and is free of the deodorant 50.

Figure 4:
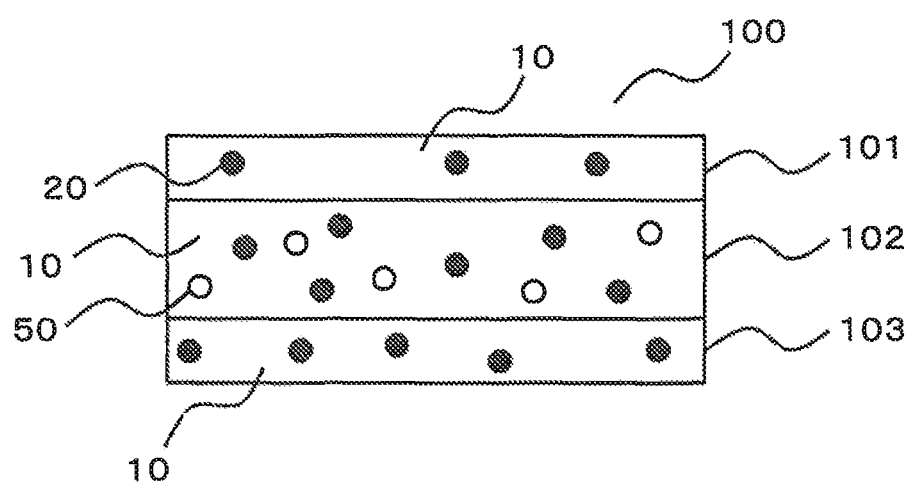
FIG. 4 is a schematic sectional view of an example of the stretchable film according to another embodiment of the present invention.

FIG. 4 is a schematic sectional view of an example of the stretchable film according to another embodiment of the present invention. In FIG. 4, the stretchable film 100 is formed of a laminate of three layers (A layer 101 and B layer 102, and C layer 103), the A layer 101 contains the olefin-based resin 10 and the filler 20, and is free of the deodorant 50, the B layer 102 contains the olefin-based resin 10, the filler 20, and the deodorant 50, and the C layer 103 contains the olefin-based resin 10 and the filler 20, and is free of the deodorant 50.

Figure 5:
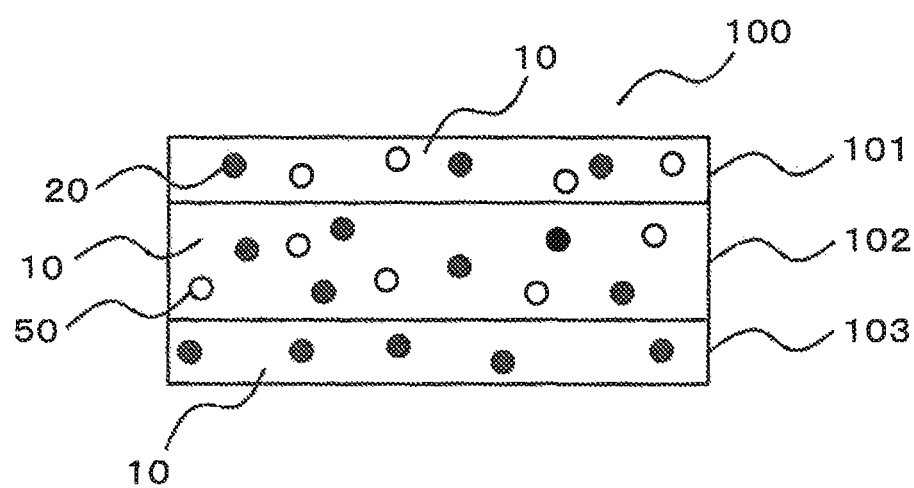
FIG. 5 is a schematic sectional view of an example of the stretchable film according to another embodiment of the present invention.

FIG. 5 is a schematic sectional view of an example of the stretchable film according to another embodiment of the present invention. In FIG. 5, the stretchable film 100 is formed of a laminate of three layers (A layer 101, B layer 102, and C layer 103), the A layer 101 contains the olefin-based resin 10, the filler 20, and the deodorant 50, the B layer 102 contains the olefin-based resin 10, the filler 20, and the deodorant 50, and the C layer 103 contains the olefin-based resin 10 and the filler 20, and is free of the deodorant 50.

Figure 6:
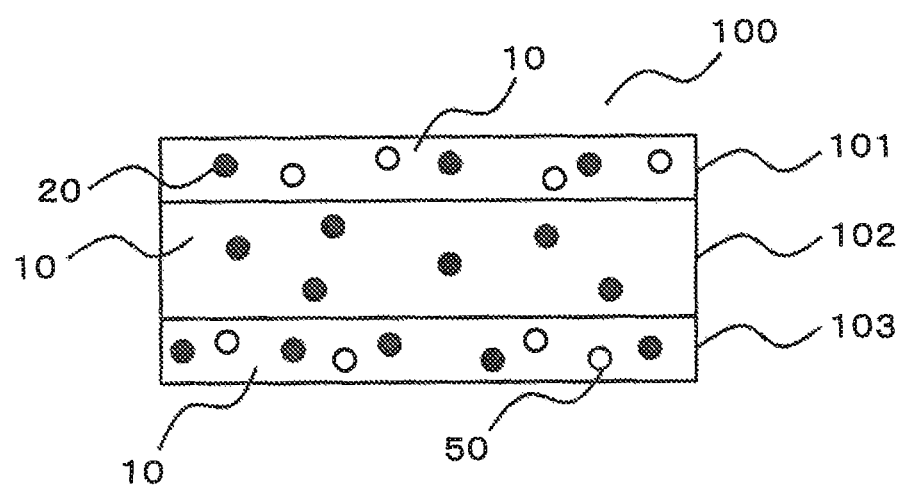
FIG. 6 is a schematic sectional view of an example of the stretchable film according to another embodiment of the present invention.

FIG. 6 is a schematic sectional view of an example of the stretchable film according to another embodiment of the present invention. In FIG. 6, the stretchable film 100 is formed of a laminate of three layers (A layer 101, B layer 102, and C layer 103), the A layer 101 contains the olefin-based resin 10, the filler 20, and the deodorant 50, the B layer 102 contains the olefin-based resin 10 and the filler 20, and is free of the deodorant 50, and the C layer 103 contains the olefin-based resin 10, the filler 20, and the deodorant 50.

Figure 7:
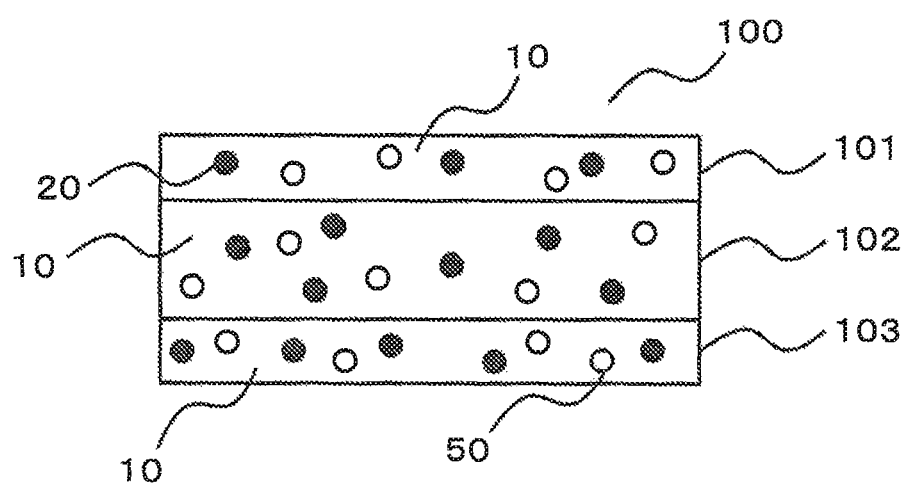
FIG. 7 is a schematic sectional view of an example of the stretchable film according to another embodiment of the present invention.

FIG. 7 is a schematic sectional view of an example of the stretchable film according to another embodiment of the present invention. In FIG. 7, the stretchable film 100 is formed of a laminate of three layers (A layer 101, B layer 102, and C layer 103), the A layer 101 contains the olefin-based resin 10, the filler 20, and the deodorant 50, the B layer 102 contains the olefin-based resin 10, the filler 20, and the deodorant 50, and the C layer 103 contains the olefin-based resin 10, the filler 20, and the deodorant 50.

The stretchable film of the present invention preferably includes the olefin-based resin.

The olefin-based resin may be only one kind of resin, or may be a blend of two or more kinds of resins.

When the stretchable film of the present invention is formed of a laminate of two or more layers, at least one kind of layer of the respective layers preferably contains an olefin-based resin, and the olefin-based resin may be only one kind of resin, or may be a blend of two or more kinds of resins. When the stretchable film of the present invention is formed of a laminate of two or more layers, each of all the layers more preferably contains an olefin-based resin, and the olefin-based resin may be only one kind of resin, or may be a blend of two or more kinds of resins.

The term "olefin-based resin" as used herein is meant to include an "olefin-based elastomer" having an elastomeric property and a "non-elastomeric olefin-based resin" free of any elastomeric property. That is, when the term "olefin-based resin" is used herein, unless particular limitative description is present, the term means that the following three cases may be present: a case in which the resin is only an "olefin-based elastomer;" a case in which the resin is only a "non-elastomeric olefin-based resin;" and a case in which the resin is a blend of an "olefin-based elastomer" and a "non-elastomeric olefin-based resin."

The olefin-based resin preferably contains an olefin-based elastomer. When the olefin-based resin contains the olefin-based elastomer, the stretchable film of the present invention may express more excellent stretchability. In addition, when the olefin-based resin contains the olefin-based elastomer, the stretchable film of the present invention may express more excellent air permeability by being combined with the filler. In addition, when the olefin-based resin contains the olefin-based elastomer, an odor generated from the stretchable film of the present invention may be suppressed.

The olefin-based elastomer may be only one kind of elastomer, or may be a blend of two or more kinds of elastomers.

When the stretchable film of the present invention contains the olefin-based elastomer, its heat stability is improved, and hence, for example, heat decomposition at the time of the production of the stretchable film of the present invention may be suppressed.

When the stretchable film of the present invention contains the olefin-based elastomer, its storage stability is improved, and hence fluctuations in physical property values during the storage of the stretchable film of the present invention may be suppressed.

When the stretchable film of the present invention contains the olefin-based elastomer, a process in the production of an elastomer layer may be simplified, and hence a processing cost may be suppressed. This is because of the following reason: when the olefin-based elastomer is adopted, resins to be used in the production of the elastomer layer may be subjected to extrusion molding while the number of kinds thereof is reduced, and hence the need for the production of a master batch may be eliminated.

When the stretchable film of the present invention is formed only of one layer, the content of the olefin-based elastomer in the olefin-based resin is preferably from 50 wt % to 100 wt %, more preferably from 70 wt % to 100 wt %, still more preferably from 90 wt % to 100 wt %, particularly preferably from 95 wt % to 100 wt %, most preferably substantially 100 wt % because the effects of the present invention are expressed to a larger extent. In the case where the stretchable film of the present invention is formed only of one layer, when the content of the olefin-based elastomer in the olefin-based resin is adjusted within the range, the stretchable film of the present invention may be excellent in oil resistance. In addition, in the case where the stretchable film of the present invention is formed only of one layer, when the content of the olefin-based elastomer in the olefin-based resin is adjusted within the range, the stretchable film of the present invention may express more excellent stretchability. In addition, in the case where the stretchable film of the present invention is formed only of one layer, when the content of the olefin-based elastomer in the olefin-based resin is adjusted within the range, the stretchable film of the present invention may express more excellent air permeability by being combined with the filler. In addition, when the content of the olefin-based elastomer in the olefin-based resin is adjusted within the range, the odor generated from the stretchable film of the present invention may be suppressed to a larger extent.

When the stretchable film of the present invention is formed of a laminate of L layers, where L represents 2 or more, the stretchable film may include (L−1) or less layers each containing no olefin-based resin (other layers) to the extent that the effects of the present invention are not impaired.

When the stretchable film of the present invention is formed of a laminate of two or more layers, the number of the layers is preferably from 2 to 10, more preferably from 2 to 5, still more preferably from 2 to 4, particularly preferably 3. When the stretchable film of the present invention is formed of a laminate of three layers, the effects of the present invention may be expressed to a larger extent. In addition, the stretchable film of the present invention may be excellent in handleability, and may be excellent in blocking resistance.

When the stretchable film of the present invention is formed of a laminate of two or more layers, all the respective layers may be of different kinds, or at least two of the layers may be of the same kind.

When the stretchable film of the present invention is formed of a laminate of two or more layers, the thickness of each layer is preferably from 2 µm to 100 µm, more preferably from 2 µm to 70 µm.

In the case where the stretchable film of the present invention is formed of a laminate of three layers, when its layer construction is represented by A layer, B layer, and C layer in the stated order, the thickness of each of the A layer and the C layer serving as surface layers is preferably from 2 µm to 40 µm, more preferably from 2 µm to 30 µm, still more preferably from 2 µm to 20 µm, particularly preferably from 2 µm to 10 µm, most preferably from 2 µm to 8 µm.

In the case where the stretchable film of the present invention is formed of a laminate of three layers, when its layer construction is represented by A layer, B layer, and C layer in the stated order, the thickness of the B layer serving as an intermediate layer is preferably from 10 µm to 70 µm, more preferably from 15 µm to 70 µm, still more preferably from 20 µm to 70 µm, particularly preferably from 30 µm to 70 µm, most preferably from 40 µm to 70 µm.

In the case where the stretchable film of the present invention is formed of a laminate of three layers, when its layer construction is represented by A layer, B layer, and C layer in the stated order, the B layer serving as an intermediate layer may be a plurality of layers. That is, in the case of a laminate of four layers represented by A layer, B layer, B' layer, and C layer in the stated order, the thickness of each layer preferably falls within the above-mentioned range while the total thickness of the B layer and the B' layer is set within the above-mentioned thickness range of the B layer.

In the case where the stretchable film of the present invention is formed of a laminate of three layers, when its layer construction is represented by A layer, B layer, and C layer in the stated order, a ratio among the thicknesses of the A layer, the B layer, and the C layer is as follows: the ratio of A layer:B layer:C layer is preferably from 1 to 30:from 40 to 98:from 1 to 30; the ratio of A layer:B layer:C layer is more preferably from 3 to 25:from 50 to 94:from 3 to 25; the ratio of A layer:B layer:C layer is still more preferably from 5 to 20:from 60 to 90:from 5 to 20; and the ratio A layer:B layer:C layer, is particularly preferably from 7 to 15:from 70 to 86:from 7 to 15. When the ratio among the thicknesses of the A layer, the B layer, and the C layer falls within the range, the effects of the present invention may be expressed to a larger extent. In addition, the stretchable film of the present invention may be more excellent in handleability, and may be more excellent in blocking resistance.

When the stretchable film of the present invention is formed of a laminate of three layers, a form in which all of the three layers each contain an olefin-based elastomer is permitted, a form in which only two of the three layers each contain an olefin-based elastomer is also permitted, and a form in which only one of the three layers contains an olefin-based elastomer is also permitted. When the stretchable film of the present invention has such construction, the effects of the present invention may be expressed to a larger extent. In addition, the stretchable film of the present invention may be more excellent in handleability, and may be more excellent in blocking resistance.

When the stretchable film of the present invention is formed of a laminate of three layers, a form in which its intermediate layer (the B layer in the foregoing) contains an olefin-based elastomer and is free of a non-elastomeric olefin-based resin is more preferred. When the stretchable film of the present invention has such form, the effects of the present invention may be expressed to a larger extent. In addition, the stretchable film of the present invention may be more excellent in handleability, and may be more excellent in blocking resistance.

When the stretchable film of the present invention is formed of a laminate of three layers, any one of the following constructions is preferred: (1) a construction "[layer containing a non-elastomeric olefin-based resin as a resin component]/[layer containing an olefin-based elastomer as a resin component]/[(layer containing the non-elastomeric olefin-based resin as a resin component];" and (2) a construction "[layer containing a blend of an olefin-based elastomer and a non-elastomeric olefin-based resin as a resin component]/[layer containing the olefin-based elastomer as a resin component]/[layer containing the blend of the olefin-based elastomer and the non-elastomeric olefin-based resin as a resin component]." When the stretchable film of the present invention has such construction, the effects of the present invention may be expressed to a larger extent. In addition, the stretchable film of the present invention may be more excellent in handleability, and may be more excellent in blocking resistance.

The non-elastomeric olefin-based resin may be only one kind of resin, or may be a blend or a copolymer of two or more kinds of resins.

In a layer containing the olefin-based elastomer as a resin component, the content of the olefin-based elastomer in the olefin-based resin in the layer is preferably from 20 wt % to 80 wt %, more preferably from 25 wt % to 75 wt %, still more preferably from 30 wt % to 70 wt %, particularly preferably from 35 wt % to 65 wt %, most preferably from 40 wt % to 60 wt % because the effects of the present invention are expressed to a larger extent. When the content of the olefin-based elastomer in the olefin-based resin in the layer containing the olefin-based elastomer as a resin component is adjusted within the range, the stretchable film of the present invention may be excellent in oil resistance. In addition, when the content of the olefin-based elastomer in the olefin-based resin in the layer containing the olefin-based elastomer as a resin component is adjusted within the range, the stretchable film of the present invention may express excellent stretchability. In addition, when the content of the olefin-based elastomer in the olefin-based resin in the layer containing the olefin-based elastomer as a resin component is adjusted within the range, the stretchable film of the present invention may express excellent air permeability by being combined with the filler. In addition, when the content of the olefin-based elastomer in the olefin-based resin in the layer containing the olefin-based elastomer as a resin component is adjusted within the range, the odor generated from the stretchable film of the present invention may be suppressed to a larger extent.

In a layer containing the non-elastomeric olefin-based resin as a resin component, the content of the non-elastomeric olefin-based resin in the olefin-based resin in the layer is preferably from 20 wt % to 80 wt %, more preferably from 25 wt % to 75 wt %, still more preferably from 30 wt % to 70 wt %, particularly preferably from 35 wt % to 65 wt %, most preferably from 40 wt % to 60 wt % because the effects of the present invention are expressed to a larger extent. When the content of the non-elastomeric olefin-based resin in the olefin-based resin in the layer containing the non-elastomeric olefin-based resin as a resin component is adjusted within the range, the effects of the present invention may be expressed to a larger extent. In addition, the stretchable film of the present invention may be excellent in handleability, and may be excellent in blocking resistance.

Examples of the olefin-based elastomer include an olefin block copolymer, an olefin random copolymer, an ethylene copolymer, a propylene copolymer, an ethylene olefin block copolymer, a propylene olefin block copolymer, an ethylene olefin random copolymer, a propylene olefin random copolymer, an ethylene propylene random copolymer, an ethylene (1-butene) random copolymer, an ethylene (1-pentene) olefin block copolymer, an ethylene (1-hexene) random copolymer, an ethylene (1-heptene) olefin block copolymer, an ethylene (1-octene) olefin block copolymer, an ethylene (1-nonene) olefin block copolymer, an ethylene (1-decene) olefin block copolymer, a propylene ethylene olefin block copolymer, an ethylene ($\alpha$-olefin) copolymer, an ethylene ($\alpha$-olefin) random copolymer, an ethylene ($\alpha$-olefin) block copolymer, amorphous polypropylene, combinations of the above-mentioned polymers and polyethylene (LLDPE, LDPE, HDPE, or the like), combinations of the above-mentioned polymers and polypropylene, and combinations thereof.

The olefin-based elastomer has a density of preferably from 0.890 $g/cm^3$ to 0.830 $g/cm^3$, more preferably from 0.888 $g/cm^3$ to 0.835 $g/cm^3$, still more preferably from 0.886 $g/cm^3$ to 0.835 $g/cm^3$, particularly preferably from 0.885 $g/cm^3$ to 0.840 $g/cm^3$, most preferably from 0.885 $g/cm^3$ to 0.845 $g/cm^3$. When the olefin-based elastomer whose density falls within the range is incorporated into a layer forming the stretchable film of the present invention, the stretchable film of the present invention may be more excellent in oil resistance. In addition, when the olefin-based elastomer whose density falls within the range is incorporated into a layer forming the stretchable film of the present invention, the stretchable film of the present invention may express more excellent stretchability. In addition, when the olefin-based elastomer whose density falls within the range is incorporated into a layer forming the stretchable film of the present invention, the stretchable film of the present invention may express more excellent air permeability by being combined with the filler. In addition, when the olefin-based elastomer whose density falls within the range is incorporated into a layer forming the stretchable film of the present invention, the odor generated from the stretchable film of the present invention may be suppressed to a larger extent.

The olefin-based elastomer has a MFR at 230° C. and 2.16 kgf of preferably from 1.0 g/10 min to 25.0 g/10 min, more preferably from 2.0 g/10 min to 23.0 g/10 min, still more preferably from 2.0 g/10 min to 21.0 g/10 min, particularly preferably from 2.0 g/10 min to 20.0 g/10 min, most preferably from 2.0 g/10 min to 19.0 g/10 min. When the olefin-based elastomer whose MFR falls within the range is incorporated into a layer forming the stretchable film of the present invention, the stretchable film of the present invention may be more excellent in oil resistance. In addition, when the olefin-based elastomer whose MFR falls within the range is incorporated into a layer forming the stretchable film of the present invention, the stretchable film of the present invention may further express more excellent stretchability. In addition, when the olefin-based elastomer whose MFR falls within the range is incorporated into a layer forming the stretchable film of the present invention, the stretchable film of the present invention may express more excellent air permeability by being combined with the filler. In addition, when the olefin-based elastomer whose MFR falls within the range is incorporated into a layer forming the stretchable film of the present invention, the odor generated from the stretchable film of the present invention may be suppressed to a larger extent.

Specifically, the olefin-based elastomer is preferably an $\alpha$-olefin-based elastomer. Of such $\alpha$-olefin-based elastomers, at least one kind selected from an ethylene-based elastomer, a propylene-based elastomer, and a 1-butene-based elastomer is more preferred. When such $\alpha$-olefin-based elastomer is adopted as the olefin-based elastomer, the stretchable film of the present invention may be more excellent in oil resistance. In addition, when such $\alpha$-olefin-based elastomer is adopted as the olefin-based elastomer, the stretchable film of the present invention may express more excellent stretchability. In addition, when such $\alpha$-olefin-based elastomer is adopted as the olefin-based elastomer, the stretchable film of the present invention may express more excellent air permeability by being combined with the filler. In addition, when such $\alpha$-olefin-based elastomer is adopted as the olefin-based elastomer, the odor generated from the stretchable film of the present invention may be suppressed to a larger extent.

Of the $\alpha$-olefin-based elastomers, the ethylene-based elastomer or the propylene-based elastomer is particularly preferred. When the ethylene-based elastomer or the propylene-based elastomer is adopted as the olefin-based elastomer, the stretchable film of the present invention may be more excellent in oil resistance. In addition, when the ethylene-based elastomer or the propylene-based elastomer is adopted as the olefin-based elastomer, the stretchable film of the present invention may express more excellent stretchability. In addition, when the ethylene-based elastomer or the propylene-based elastomer is adopted as the olefin-based elastomer, the stretchable film of the present invention may express more excellent air permeability by being combined with the filler. In addition, when the ethylene-based elastomer or the propylene-based elastomer is adopted as the olefin-based elastomer, the odor generated from the stretchable film of the present invention may be suppressed to a larger extent.

Of the $\alpha$-olefin-based elastomers, the propylene-based elastomer is particularly preferred. When the stretchable film of the present invention includes the propylene-based elastomer, its heat stability is improved, and hence, for example, heat decomposition at the time of the production of the stretchable film of the present invention may be suppressed. In addition, when the stretchable film of the present invention includes the propylene-based elastomer, its storage stability is improved, and hence fluctuations in physical property values during the storage of the stretchable film of the present invention may be suppressed.

When the stretchable film of the present invention includes the propylene-based elastomer, a production process for the stretchable film of the present invention may be simplified, and hence processing cost therefor may be suppressed. This is because the adoption of the propylene-based elastomer enables extrusion molding at the time of the production of the stretchable film of the present invention, and hence may eliminate the need for the production of a master batch.

Examples of the propylene-based elastomer include a propylene copolymer, a propylene olefin block copolymer, a propylene olefin random copolymer, a propylene ethylene olefin block copolymer, and amorphous polypropylene.

The propylene-based elastomer has a MFR at 230° C. and 2.16 kgf of preferably from 0.1 g/10 min to 18 g/10 min, more preferably from 0.5 g/10 min to 15 g/10 min, still more preferably from 1.0 g/10 min to 10 g/10 min, particularly preferably from 1.5 g/10 min to 7 g/10 min, most preferably from 2 g/10 min to 5 g/10 min. When the MFR of the propylene-based elastomer is set within the range, the stretchable film of the present invention may express more excellent stretchability. In addition, when the MFR of the propylene-based elastomer is set within the range, the stretchable film of the present invention may express more excellent air permeability by being combined with the filler.

The α-olefin-based elastomer is also available as a commercial product. Examples of such commercial product include some products in the "Tafmer" (trademark) series (e.g., Tafmer PN-2070 and Tafmer PN-3560) manufactured by Mitsui Chemicals, Inc., and some products in the "Vistamaxx" (trademark) series (e.g., Vistamaxx 6202 and Vistamaxx 7010) manufactured by Exxon Mobil Corporation.

The α-olefin-based elastomer is preferably produced by using a metallocene catalyst. When the α-olefin-based elastomer produced by using the metallocene catalyst is adopted, the stretchable film of the present invention may be more excellent in oil resistance. In addition, when the α-olefin-based elastomer produced by using the metallocene catalyst is adopted, the stretchable film of the present invention may express more excellent stretchability. In addition, when the α-olefin-based elastomer produced by using the metallocene catalyst is adopted, the stretchable film of the present invention may express more excellent air permeability by being combined with the filler. In addition, when the α-olefin-based elastomer produced by using the metallocene catalyst is adopted, the odor generated from the stretchable film of the present invention may be suppressed to a larger extent.

Examples of the non-elastomeric oilefin-based resin include an α-olefin homopolymer, a copolymer of two or more kinds of α-olefins, block polypropylene, random polypropylene, and a copolymer of one or two or more kinds of α-olefins and any other vinyl monomer. A copolymerization form in any such copolymer is, for example, a block form or a random form.

Examples of the α-olefin include α-olefins each having 2 to 12 carbon atoms. Examples of such α-olefin include ethylene, propylene, 1-butene, and 4-methyl-1-pentene.

Examples of the α-olefin homopolymer include polyethylene (PE), homopolypropylene (PP), poly(1-butene), and poly(4-methyl-1-pentene).

Examples of the polyethylene (PE) include low-density polyethylene (LDPE), linear low-density polyethylene (LLDPE), medium-density polyethylene (MDPE), and high-density polyethylene (HDPE).

The structure of the homopolypropylene (PP) may be any one of isotactic, atactic, and syndiotactic structures.

The non-elastomeric olefin-based resin preferably contains at least one kind selected from polyethylene (PE) and homopolypropylene (PP), and more preferably contains at least one kind selected from high-density polyethylene (HDPE), low-density polyethylene (LDPE), linear low-density polyethylene (LLDPE), and homopolypropylene (PP) because the effects of the present invention may be expressed to a larger extent. When the non-elastomeric olefin-based resin contains at least one kind selected from the high-density polyethylene (HDPE), the low-density polyethylene (LDPE), the linear low-density polyethylene (LLDPE), and the homopolypropylene (PP), a stretchable film more excellent in handleability may be provided. The content of at least one kind selected from the high-density polyethylene (HDPE), the low-density polyethylene (LDPE), the linear low-density polyethylene (LLDPE), and the homopolypropylene (PP) in the non-elastomeric olefin-based resin is preferably from 50 wt % to 100 wt %, more preferably from 70 wt % to 100 wt %, still more preferably from 80 wt % to 100 wt %, still further more preferably from 90 wt % to 100 wt %, particularly preferably from 95 wt % to 100 wt %, most preferably substantially 100 wt % because the effects of the present invention may be expressed to a larger extent.

Examples of the copolymer of two or more kinds of α-olefins include an ethylene/propylene copolymer, an ethylene/1-butene copolymer, an ethylene/propylene/1-butene copolymer, a copolymer of ethylene/α-olefin having 5 to 12 carbon atoms, and a copolymer of propylene/α-olefin having 5 to 12 carbon atoms.

Examples of the copolymer of one or two or more kinds of α-olefins and any other vinyl monomer include an ethylene/vinyl acetate copolymer, an ethylene/acrylic acid alkyl ester copolymer, an ethylene/methacrylic acid alkyl ester copolymer, and an ethylene-non-conjugated diene copolymer.

A commercial product may be used as the non-elastomeric olefin-based resin.

The stretchable film of the present invention preferably includes the filler. The filler is preferably at least one kind selected from inorganic particles and organic particles. The filler may be only one kind of filler, or may be two or more kinds of fillers. When the stretchable film of the present invention contains the filler, the stretchable film of the present invention may express more excellent air permeability.

When the stretchable film of the present invention is formed of a laminate of two or more layers, the filler is preferably incorporated into at least one layer in the layers forming the laminate, and is more preferably incorporated into each of all the layers forming the laminate.

Examples of the inorganic particles include talc, titanium oxide, calcium oxide, magnesium oxide, zinc oxide, titanium oxide, calcium carbonate, silica, clay, mica, barium sulfate, whisker, and magnesium hydroxide.

Examples of the organic particles include acrylic beads, styrene beads, and silicone resin particles.

Any appropriate average particle diameter may be adopted as the average particle diameter of the filler to the extent that the effects of the present invention are not impaired. The lower limit of such average particle diameter of the filler is preferably 0.5 μm or more, more preferably 0.6 μm or more, still more preferably 0.7 μm or more, and the upper limit thereof is preferably 50 μm or less, more preferably 30 μm or less, still more preferably 10 μm or less, particularly preferably 5 μm or less. When the average particle diameter of the filler is adjusted within the range, the stretchable film of the present invention may express even more excellent air permeability.

Any appropriate content may be adopted as the content of the filler to the extent that the effects of the present invention are not impaired. The lower limit of such content of the filler is preferably 50 parts by weight or more, more preferably 70 parts by weight or more, still more preferably 100 parts by weight or more with respect to 100 parts by weight of the olefin-based resin in the stretchable film, and the upper limit thereof is preferably 400 parts by weight or less, more preferably 350 parts by weight or less, still more preferably 300 parts by weight or less with respect thereto. When the content of the filler is adjusted within the range, the stretchable film of the present invention may express even more excellent air permeability.

When the stretchable film of the present invention is formed of a laminate of two or more layers, the lower limit of the content of the filler in each layer forming the laminate is preferably 50 parts by weight or more, more preferably 70 parts by weight or more, still more preferably 100 parts by weight or more with respect to 100 parts by weight of the olefin-based resin in the layer, and the upper limit thereof is preferably 400 parts by weight or less, more preferably 350 parts by weight or less, still more preferably 300 parts by weight or less with respect thereto. When the content of the filler is adjusted within the range, the stretchable film of the present invention may express even more excellent air permeability.

The filler may be coated with a releasing agent for preventing aggregation. Examples of such releasing agent include a fatty acid amide-based releasing agent, a silicone-based releasing agent, a fluorine-based releasing agent, and a long-chain alkyl-based releasing agent. Of those, a fatty acid amide-based releasing agent is preferred, and a saturated fatty acid bisamide is more preferred. Any appropriate usage amount may be adopted as the usage amount of the releasing agent.

The stretchable film of the present invention may contain any appropriate other component to the extent that the effects of the present invention are not impaired. The other component may be only one kind of component, or may be two or more kinds of components. Examples of such other component include a UV absorber, a heat stabilizer, a releasing agent, a lubricant, a colorant (e.g., a dye), an antioxidant, an anti-build up agent, an antiblocking agent, a foaming agent, other polymers, a tackifier, a plasticizer, an antidegradant, an antistatic agent, and a light stabilizer. Those components may be used alone or in combination thereof.

Examples of the UV absorber include a benzotriazole-based compound, a benzophenone-based compound, and a benzoate-based compound. Any appropriate content may be adopted as the content of the UV absorber as long as the UV absorber does not bleed out at the time of the forming.

Examples of the heat stabilizer include a hindered amine-based compound, a phosphorus-based compound, and a cyanoacrylate-based compound. Any appropriate content may be adopted as the content of the heat stabilizer as long as the heat stabilizer does not bleed out at the time of the forming.

Examples of the releasing agent include a fatty acid amide-based releasing agent, a silicone-based releasing agent, a fluorine-based releasing agent, and a long-chain alkyl-based releasing agent. Of those, a fatty acid amide-based releasing agent is preferred from the viewpoint that a peeling layer more excellent in balance between peelability and resistance against contamination due to bleedout may be formed, and a saturated fatty acid bisamide is more preferred. Any appropriate content may be adopted as the content of the releasing agent.

The stretchable film of the present invention is preferably obtained by subjecting an unstretched film to a stretching treatment. Such stretching treatment of the stretched film may be referred to as "pre-extension". When the unstretched film is subjected to the stretching treatment, the stretchable film of the present invention may express more excellent stretchability. In addition, when the unstretched film is subjected to the stretching treatment, the stretchable film of the present invention may express more excellent air permeability by being combined with the filler.

The pre-extension is pre-extension having the following meaning: the stretchable film of the present invention is extended in advance in consideration of the fact that the stretchable film is extended again (post-extension) in its final use (e.g., at the time of the production of a diaper and at the time of the use of the diaper).

The pre-extension is preferably performed after the stretchable film of the present invention has been produced and sufficiently solidified.

The pre-extension may be performed on the entirety of the original length or width in at least one direction, or may be performed on part of the original length or width. In addition, the pre-extension may be performed in any appropriate direction. The pre-extension is preferably performed on the original length or width in at least one direction.

The extension degree of the pre-extension is preferably 1.5 times or more and less than 2.5 times (typically 2.0 times), more preferably 2.5 times or more and less than 3.5 times (typically 3.0 times), still more preferably 3.5 times or more and less than 4.5 times (typically 4.0 times), particularly preferably 4.5 times or more and less than 5.5 times (typically 5.0 times). For example, 2.0-time pre-extension means that when the original length of the stretchable film is represented by L, the stretchable film is extended (sometimes referred to as "stretched") to have a length of 2 L. The stretchable film of the present invention may express more excellent stretchability by being pre-extended to such extension degree. In addition, when the stretchable film of the present invention is pre-extended to such extension degree, the stretchable film may express more excellent air permeability by being combined with the filler.

The pre-extension is preferably performed at a temperature less than the melting point of the olefin-based resin. The stretchable film of the present invention may express more excellent stretchability by being pre-extended at such temperature. In addition, when the stretchable film of the present invention is pre-extended at such temperature, the stretchable film may express more excellent air permeability by being combined with the filler.

When the stretchable film of the present invention is preferably pre-extended as described above, the olefin-based resin undergoes plastic deformation or is extended beyond the brittle fracture point of the olefin-based resin, and hence the film may express more excellent stretchability.

<<Production of Stretchable Film>>

Any appropriate method may be adopted as a method of producing the stretchable film of the present invention to the extent that the effects of the present invention are not impaired. The stretchable film is preferably obtained by: producing an unstretched film by any appropriate method; and then subjecting the unstretched film to a stretching treatment. The stretching treatment is preferably performed after the unstretched film has been produced and sufficiently solidified. Details about the stretching treatment are as described in the foregoing.

A method of producing the unstretched film is typically, for example, a method involving molding materials for the stretchable film of the present invention with a T-die molding machine to produce the unstretched film. For example, a rolled body of the stretchable film of the present invention may be produced by: extruding the materials for the stretchable film with the T-die molding machine from its T-die; and then winding the extruded materials in a roll shape. In addition to the T-die method involving using the T-die, an inflation method or the like may also be adopted.

<<Application of Stretchable Film>>

The stretchable film of the present invention may be used in any appropriate article in which the effects of the present invention may be effectively utilized. That is, the article of the present invention includes the stretchable film of the present invention. A typical example of such article is a sanitary article. Examples of such sanitary article include a diaper (in particular, such a diaper that the stretchable film of the present invention is used as a stretchable material in an ear portion or a stretchable material in the opening portion of waist surroundings or leg surroundings (a waist band or a gather)), a supporter, and a mask.

EXAMPLES

The present invention is hereinafter specifically described by way of Examples. However, the present invention is by no means limited to these Examples. Test and evaluation methods in Examples and the like are as described below. In addition, "part(s)" means "part(s) by weight" and "%" means "wt %" unless otherwise stated.

<Method of Evaluating Stretchability>

Figure 8:
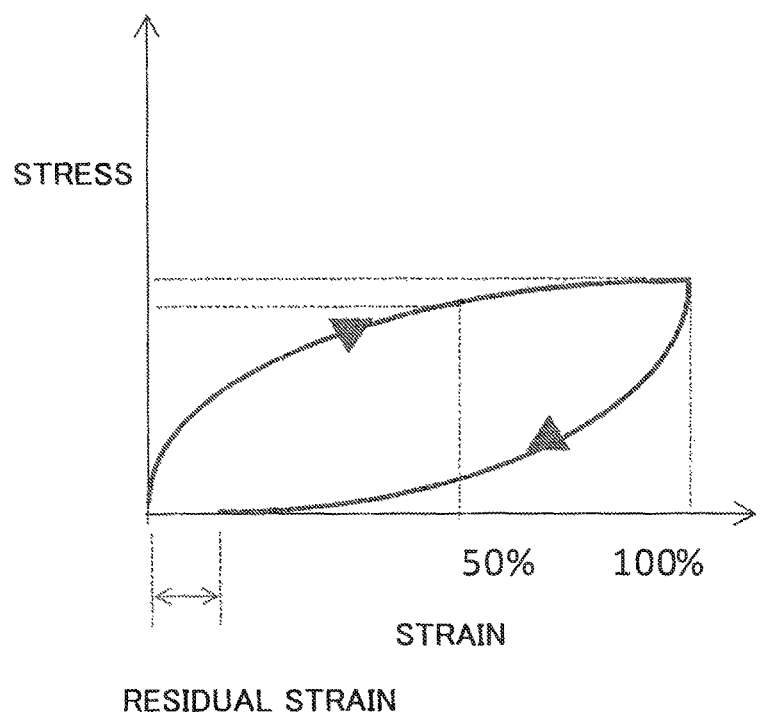
FIG. 8 is a graphical representation for showing a relationship between the stress and strain of a hysteresis test at the time of the measurement of a residual strain.

Such a hysteresis test as shown in FIG. 8 was performed on a test piece having a width of 20 mm by pulling the test piece from a chuck-to-chuck distance of 30 mm to a chuck-to-chuck distance of 60 mm at a tensile rate of 50 mm/min and holding the test piece for 1 minute, followed by the removal of the tension of the chuck-to-chuck distance, and a residual strain at the time of the removal of the tension of the chuck-to-chuck distance was measured. With regard to the residual strain measurement, when a produced film was a uniaxially stretched film, its tensile direction was set to a direction perpendicular to the direction of the stretching (a CD direction when the film was stretched in a machine (MD) direction).

A case in which the residual strain was less than 10 mm was indicated by Symbol "○".

A case in which the residual strain was 10 mm or more was indicated by Symbol "x".

<Method of evaluating Air Permeability>

An air permeability measured with an Oken-type air permeability meter (sec/100 cc) (manufactured by Asahi Seiko Co., Ltd., product name: EG01-7-7MR) was used as an indicator of air permeability.

A film having an air permeability of less than 9,999 sec/100 cc was indicated by Symbol "○" (judged to have sufficient air permeability).

A film having an air permeability of 9,999 sec/100 cc or more and less than 99, 999 sec/100 cc was indicated by Symbol "Δ" (judged to have moderate air permeability).

A film having an air permeability of 99, 999 sec/100 cc or more was indicated by Symbol "x" (judged to have no air permeability).

In Table 1, the column "Film as it is" means that the air permeability of a produced film was measured while the film was kept as it was. In addition, in Table 1, the column "Twice in transverse direction" means that the air permeability of a produced film was measured under a state in which the film was extended twice in its transverse direction.

<Method of evaluating Deodorizing Property>

A deodorization efficiency was calculated as described in the following (i) (Example 1 and Comparative Example 1) or (ii) (Examples 2 to 4 and Comparative Example 2).

(i) A stretchable film serving as a measurement object, which had been cut into a size measuring 140 mm by 200 mm, was loaded into a Tedlar bag having a volume of 3 L in a thermohygrostatic chamber at 20° C. and 65% RH. Next, 3 L of odorless air that had been passed through activated carbon was sealed in the Tedlar bag, and then an odor gas was injected into the Tedlar bag so that a predetermined initial gas concentration P was obtained (an initial gas concentration of 100 ppm was obtained for ammonia, and an initial gas concentration of 4 ppm was obtained for hydrogen sulfide). After that, a gas concentration was monitored with a gas detector tube (manufactured by Gastec Corporation) with time, and a gas concentration Q 3 hours after the start of the monitoring was measured. $[(P-Q)/P] \times 100=X$ (%) was calculated, and the X (%) was defined as a gas concentration reduction ratio. Meanwhile, the stretchable film serving as a measurement object was subjected to the same measurement without being loaded into the Tedlar bag, and a gas concentration $Q_0$ 3 hours after the start of the measurement was measured. $[(P-Q_0)/P] \times 100=Y$ (%) was calculated, and the Y (%) was defined as a blank gas concentration reduction ratio. (X−Y) (%) was calculated from the gas concentration reduction ratio X (%) and the blank gas concentration reduction ratio Y (%) thus obtained, and was defined as the deodorization efficiency.

(ii) A stretchable film serving as a measurement object, which had been cut into a size measuring 100 mm by 100 mm, was loaded into Smart Bag PA having a volume of 5 L (manufactured by GL Sciences Inc.) in a thermohygrostatic chamber at 25° C. and 20% RH. Next, 2 L of odorless air that had been passed through activated carbon was sealed in the Smart Bag PA, and then an odor gas was injected into the Smart Bag PA so that a predetermined initial gas concentration P was obtained (an initial gas concentration of 100 ppm was obtained for ammonia, and an initial gas concentration of 4 ppm was obtained for hydrogen sulfide). After that, a gas concentration was monitored with a gas detector tube (manufactured by Gastec Corporation) with time, and a gas concentration Q 3 hours after the start of the monitoring was measured. $[(P-Q)/P] \times 100=X$ (%) was calculated, and the X (%) was defined as a gas concentration reduction ratio. Meanwhile, the stretchable film serving as a measurement object was subjected to the same measurement without being loaded into the Smart Bag PA, and a gas concentration $Q_0$ 3 hours after the start of the measurement was measured. $[(P-Q_0)/P] \times 100=Y$ (%) was calculated, and the Y (%) was defined as a blank gas concentration reduction ratio. (X−Y) (%) was calculated from the gas concentration reduction ratio X (%) and the blank gas concentration reduction ratio Y (%) thus obtained, and was defined as the deodorization efficiency.

A deodorization efficiency of 10% or more was indicated by Symbol "○" (a deodorizing property was judged to be extremely satisfactory).

A deodorization efficiency of 1% or more and less than 10% was indicated by Symbol "Δ" (a deodorizing property was judged to be satisfactory).

A deodorization efficiency of less than 1% was indicated by Symbol "x" (a deodorizing property was judged to be unsatisfactory).

Example 1

100 Parts by weight of polyethylene (HDPE) (manufactured by Tosoh Corporation, product name: Nipolon Hard 1000), 150 parts by weight of calcium carbonate (average particle diameter=1.1 μm), 3 parts by weight of silicon dioxide, and 1 part by weight of zinc oxide were loaded into a surface layer extruder. 100 Parts by weight of amorphous PP (manufactured by Exxon Mobil Corporation, product name: Vistamaxx 6202), 150 parts by weight of calcium carbonate (average particle diameter=1.1 μm), 3 parts by weight of silicon dioxide, and 1 part by weight of zinc oxide were loaded into an intermediate layer extruder. The materials were co-extruded in three layers (surface layer/intermediate layer/surface layer) from the T-dies of the extruders to produce an unstretched film (1) having a thickness of 80 μm.

Next, the unstretched film (1) was stretched in its transverse direction at a ratio of 3.8 times to provide a stretchable film (1).

The results are shown in Table 1.

Example 2

100 Parts by weight of polyethylene (HDPE) (manufactured by Tosoh Corporation, product name: Nipolon Hard 4020), 150 parts by weight of calcium carbonate (average particle diameter=1.1 μm), 3 parts by weight of silicon dioxide, and 1 part by weight of zinc oxide were loaded into a surface layer extruder. 100 Parts by weight of amorphous PP (manufactured by Exxon Mobil Corporation, product name: Vistamaxx 6102), 150 parts by weight of calcium carbonate (average particle diameter=1.1 μm), 3 parts by weight of silicon dioxide, and 1 part by weight of zinc oxide were loaded into an intermediate layer extruder. The materials were co-extruded in three layers (surface layer/intermediate layer/surface layer) from the T-dies of the extruders to produce an unstretched film (2) having a thickness of 60 μm.

Next, the unstretched film (2) was stretched in its transverse direction at a ratio of 3.8 times to provide a stretchable film (2).

The results are shown in Table 1.

Example 3

100 Parts by weight of polyethylene (HDPE) (manufactured by Tosoh Corporation, product name: Nipolon Hard 4020), 150 parts by weight of calcium carbonate (average particle diameter=1.1 μm), 3 parts by weight of silicon dioxide, and 1 part by weight of zinc oxide were loaded into a surface layer extruder. 100 Parts by weight of amorphous PP (manufactured by Exxon Mobil Corporation, product name: Vistamaxx 6102) and 150 parts by weight of calcium carbonate (average particle diameter=1.1 μm) were loaded into an intermediate layer extruder. The materials were co-extruded in three layers (surface layer/intermediate layer/surface layer) from the T-dies of the extruders to produce an unstretched film (3) having a thickness of 60 μm.

Next, the unstretched film (3) was stretched in its transverse direction at a ratio of 3.8 times to provide a stretchable film (3).

The results are shown in Table 1.

Example 4

100 Parts by weight of polyethylene (HDPE) (manufactured by Tosoh Corporation, product name: Nipolon Hard 4020) and 150 parts by weight of calcium carbonate (average particle diameter=1.1 μm) were loaded into a surface layer extruder. 100 Parts by weight of amorphous PP (manufactured by Exxon Mobil Corporation, product name: Vistamaxx 6102), 150 parts by weight of calcium carbonate (average particle diameter=1.1 μm), 3 parts by weight of silicon dioxide, and 1 part by weight of zinc oxide were loaded into an intermediate layer extruder. The materials were co-extruded in three layers (surface layer/intermediate layer/surface layer) from the T-dies of the extruders to produce an unstretched film (4) having a thickness of 60 μm.

Next, the unstretched film (4) was stretched in its transverse direction at a ratio of 3.8 times to provide a stretchable film (4).

The results are shown in Table 1.

Comparative Example 1

100 Parts by weight of polyethylene (HDPE) (manufactured by Tosoh Corporation, product name: Nipolon Hard 1000) and 150 parts by weight of calcium carbonate (average particle diameter=1.1 μm) were loaded into a surface layer extruder. 100 Parts by weight of amorphous PP (manufactured by Exxon Mobil Corporation, product name: Vistamaxx 6202) and 150 parts by weight of calcium carbonate (average particle diameter=1.1 μm) were loaded into an intermediate layer extruder. The materials were co-extruded in three layers (surface layer/intermediate layer/surface layer) from the T-dies of the extruders to produce an unstretched film (C1) having a thickness of 80 μm.

Next, the unstretched film (C1) was stretched in its transverse direction at a ratio of 3.8 times to provide a stretchable film (C1).

The results are shown in Table 1.

Comparative Example 2

100 Parts by weight of polyethylene (HDPE) (manufactured by Tosoh Corporation, product name: Nipolon Hard 4020) and 150 parts by weight of calcium carbonate (average particle diameter=1.1 μm) were loaded into a surface layer extruder. 100 Parts by weight of amorphous PP (manufactured by Exxon Mobil Corporation, product name: Vistamaxx 6102) and 150 parts by weight of calcium carbonate (average particle diameter=1.1 μm) were loaded into an intermediate layer extruder. The materials were co-extruded in three layers (surface layer/intermediate layer/surface layer) from the T-dies of the extruders to produce an unstretched film (C2) having a thickness of 60 μm.

Next, the unstretched film (C2) was stretched in its transverse direction at a ratio of 3.8 times to provide a stretchable film (C2).

The results are shown in Table 1.

TABLE 1

| | | Formulation | | | | Air permeability | | | Deodorizing property | | | |
|---|---|---|---|---|---|---|---|---|---|---|---|---|
| | | Olefin-based resin (parts(s) by weight) | Filler (parts(s) by weight) | Deodorant (parts(s) by weight) | | Film as it is | Twice in transverse direction | Strech-ability | Film as it is | | Twice in transverse direction | |
| | | | | | | | | | H₂S | NH₃ | H₂S | NH₃ |
| Example 1 | Surface layer (10%) | Nipolon Hard 1000 (100) | Calcium carbonate (150) | Silicon dioxide (3) | Zinc oxide (1) | Δ | ○ | ○ | ○ | ○ | ○ | ○ |
| | Intermediate layer (80%) | Vistamaxx 6202 (100) | Calcium carbonate (150) | Silicon dioxide (3) | Zinc oxide (1) | | | | | | | |
| | Surface layer (10%) | Nipolon Hard 1000 (100) | Calcium carbonate (150) | Silicon dioxide (3) | Zinc oxide (1) | | | | | | | |
| Example 2 | Surface layer (10%) | Nipolon Hard 4020 (100) | Calcium carbonate (150) | Silicon dioxide (3) | Zinc oxide (1) | Δ | ○ | ○ | ○ | ○ | ○ | ○ |
| | Intermediate layer (80%) | Vistamaxx 6102 (100) | Calcium carbonate (150) | Silicon dioxide (3) | Zinc oxide (1) | | | | | | | |
| | Surface layer (10%) | Nipolon Hard 4020 (100) | Calcium carbonate (150) | Silicon dioxide (3) | Zinc oxide (1) | | | | | | | |
| Example 3 | Surface layer (10%) | Nipolon Hard 4020 (100) | Calcium carbonate (150) | Silicon dioxide (3) | Zinc oxide (1) | ○ | ○ | ○ | × | ○ | ○ | ○ |
| | Intermediate layer (80%) | Vistamaxx 6102 (100) | Calcium carbonate (150) | None | None | | | | | | | |
| | Surface layer (10%) | Nipolon Hard 4020 (100) | Calcium carbonate (150) | Silicon dioxide (3) | Zinc oxide (1) | | | | | | | |
| Example 4 | Surface layer (10%) | Nipolon Hard 4020 (100) | Calcium carbonate (150) | None | None | Δ | ○ | ○ | ○ | ○ | ○ | ○ |
| | Intermediate layer (80%) | Vistamaxx 6102 (100) | Calcium carbonate (150) | Silicon dioxide (3) | Zinc oxide (1) | | | | | | | |
| | Surface layer (10%) | Nipolon Hard 4020 (100) | Calcium carbonate (150) | None | None | | | | | | | |
| Comparative Example 1 | Surface layer (10%) | Nipolon Hard 1000 (100) | Calcium carbonate (150) | None | None | Δ | ○ | ○ | × | × | × | × |
| | Intermediate layer (80%) | Vistamaxx 6202 (100) | Calcium carbonate (150) | None | None | | | | | | | |
| | Surface layer (10%) | Nipolon Hard 1000 (100) | Calcium carbonate (150) | None | None | | | | | | | |
| Comparative Example 2 | Surface layer (10%) | Nipolon Hard 4020 (100) | Calcium carbonate (150) | None | None | ○ | ○ | ○ | × | ○ | × | ○ |
| | Intermediate layer (80%) | Vistamaxx 6102 (100) | Calcium carbonate (150) | None | None | | | | | | | |
| | Surface layer (10%) | Nipolon Hard 4020 (100) | Calcium carbonate (150) | None | None | | | | | | | |

INDUSTRIAL APPLICABILITY

The stretchable film of the present invention may be used in any appropriate article in which the effects of the present invention may be effectively utilized. That is, the article of the present invention includes the stretchable film of the present invention. A typical example of such article is a sanitary article. Examples of such sanitary article include a diaper (in particular, such a diaper that the stretchable laminate of the present invention is used as a stretchable material in an ear portion or a stretchable material in the opening portion of waist surroundings or leg surroundings (a waist band or a gather)), a supporter, and a mask.

REFERENCE SIGNS LIST

Olefin-based resin 10
Filler 20
Void 30
Deodorant 50
Stretchable film 100
A layer 101
B layer 102
C layer 103

The invention claimed is:

1. A stretchable film having stretchability, comprising a chemical adsorption deodorant, the chemical adsorption deodorant containing silicon dioxide and zinc oxide, and a content ratio between silicon dioxide and zinc oxide in the chemical adsorption deodorant is from 5:95 to 95:5 in terms of weight ratio.

2. The stretchable film according to claim 1, wherein a total content of silicon dioxide and zinc oxide in the chemical adsorption deodorant is from 50 wt % to 100 wt %.

3. The stretchable film according to claim 1, wherein a content ratio between silicon dioxide and zinc oxide in the chemical adsorption deodorant is from 60:40 to 80:20 in terms of weight ratio.

4. The stretchable film according to claim 1, further comprising:
   an olefin-based resin; and
   a filler.

5. The stretchable film according to claim 4, wherein the filler comprises at least one kind selected from inorganic particles and organic particles.

6. The stretchable film according to claim 5, wherein the filler comprises inorganic particles.

7. The stretchable film according to claim 6, wherein the inorganic particles comprise at least one kind selected from talc, titanium oxide, calcium oxide, magnesium oxide, zinc oxide, titanium oxide, calcium carbonate, silica, clay, mica, barium sulfate, whisker, and magnesium hydroxide.

8. The stretchable film according to claim 7, wherein the inorganic particles comprise calcium carbonate.

9. The stretchable film according to claim 1, wherein the stretchable film is obtained by subjecting an unstretched film to a stretching treatment.

10. The stretchable film according to claim 1, wherein the stretchable film is formed of a laminate of two or more layers, and the deodorant is incorporated into at least one layer of the layers forming the laminate.

11. The stretchable film according to claim 10, wherein the deodorant is incorporated into at least one layer of outer layers.

12. The stretchable film according to claim 10, wherein the stretchable film is formed of a laminate of three layers.

13. The stretchable film according to claim 12, wherein when a layer construction of the laminate is represented by A layer, B layer, and C layer in the stated order, the deodorant is incorporated into the A layer only, the B layer only, the C layer only, both of the A layer and the B layer, both of the B layer and the C layer, both of the A layer and the C layer, or all of the A layer, the B layer, and the C layer.

14. The stretchable film according to claim 13, wherein the deodorant is incorporated into each of all of the A layer, the B layer, and the C layer.

15. The stretchable film according to claim 1, wherein the stretchable film is formed of a laminate of three layers, and when a layer construction of the laminate is represented by A layer, B layer, and C layer in the stated order, the A layer and the C layer serving as surface layers each have a thickness of from 2 μm to 40 μm.

16. The stretchable film according to claim 15, wherein the stretchable film is formed of a laminate of three layers, and when a layer construction of the laminate is represented by A layer, B layer, and C layer in the stated order, the B layer serving as an intermediate layer has a thickness of from 10 μm to 70 μm.

17. The stretchable film according to claim 15, wherein a total content of silicon dioxide and zinc oxide in the chemical adsorption deodorant is from 50 wt % to 100 wt %.

18. The stretchable film according to claim 15, wherein a content ratio between silicon dioxide and zinc oxide in the chemical adsorption deodorant is from 60:40 to 80:20 in terms of weight ratio.

19. The stretchable film according to claim 1, wherein the stretchable film has a deodorization efficiency for each of ammonia and hydrogen sulfide 3 hours after a start of a deodorization test, the deodorization efficiency being measured by a detector tube method, of 10% or more, provided that the deodorization efficiency is calculated as described in the following Measurement method (i) or (ii);

Measurement method (i) The stretchable film serving as a measurement object, which has been cut into a size measuring 140 mm by 200 mm, is loaded into a Tedlar bag having a volume of 3 L in a thermohygrostatic chamber at 20° C. and 65% RH; next, 3 L of odorless air that has been passed through activated carbon is sealed in the Tedlar bag, and then an odor gas is injected into the Tedlar bag so that a predetermined initial gas concentration P is obtained (an initial gas concentration of 100 ppm is obtained for ammonia, and an initial gas concentration of 4 ppm is obtained for hydrogen sulfide); after that, a gas concentration is monitored with a gas detector tube (manufactured by Gastec Corporation) with time, and a gas concentration Q 3 hours after a start of the monitoring is measured; $[(P-Q)/P] \times 100 = X$ (%) is calculated, and the X (%) is defined as a gas concentration reduction ratio; meanwhile, the stretchable film serving as a measurement object is subjected to the same measurement without being loaded into the Tedlar bag, and a gas concentration $Q_0$ 3 hours after a start of the measurement is measured; $[(P-Q_0)/P] \times 100 = Y$ (%) is calculated, and the Y (%) is defined as a blank gas concentration reduction ratio; and (X−Y) (%) is calculated from the gas concentration reduction ratio X (%) and the blank gas concentration reduction ratio Y (%) thus obtained, and is defined as the deodorization efficiency;

Measurement method (ii): The stretchable film serving as a measurement object, which has been cut into a size measuring 100 mm by 100 mm, is loaded into Smart Bag PA having a volume of 5 L (manufactured by GL Sciences Inc.) in a thermohygrostatic chamber at 25° C. and 20% RH; next, 2 L of odorless air that has been passed through activated carbon is sealed in the Smart Bag PA, and then an odor gas is injected into the Smart Bag PA so that a predetermined initial gas concentration P is obtained (an initial gas concentration of 100 ppm is obtained for ammonia, and an initial gas concentration of 4 ppm is obtained for hydrogen sulfide); after that, a gas concentration is monitored with a gas detector tube (manufactured by Gastec Corporation) with time, and a gas concentration Q 3 hours after a start of the monitoring is measured; $[(P-Q)/P] \times 100 = X$ (%) is calculated, and the X (%) is defined as a gas concentration reduction ratio; meanwhile, the stretchable film serving as a measurement object is subjected to the same measurement without being loaded into the Smart Bag PA, and a gas concentration $Q_0$ 3 hours after a start of the measurement is measured; $[(P-Q_0)/P] \times 100 = Y$ (%) is calculated, and the Y (%) is defined as a blank gas concentration reduction ratio; and (X−Y) (%) is calculated from the gas concentration reduction ratio X (%) and the blank gas concentration reduction ratio Y (%) thus obtained, and is defined as the deodorization efficiency.

20. The stretchable film according to claim 1, wherein the stretchable film has an air permeability measured with an Oken-type air permeability meter of less than 99,999 sec/100 cc.

21. The stretchable film according to claim 1, wherein the stretchable film has an extension direction in which an air permeability measured with an Oken-type air permeability meter under a state in which the film is extended by 100% becomes less than 60,000 sec/100 cc.

22. The stretchable film according to claim 1, wherein the stretchable film has a tensile direction in which a residual strain in the following case becomes 10 mm or less: in a hysteresis test, a test piece of the film having a width of 20 mm is pulled from a chuck-to-chuck distance of 30 mm to a chuck-to-chuck distance of 60 mm at a tensile rate of 50 mm/min and held for 1 minute, and then the tension of the chuck-to-chuck distance is removed.

23. The stretchable film according to claim 1, wherein the stretchable film is included in a sanitary article.

24. An article, comprising the stretchable film of claim 1.

25. A stretchable film having stretchability, comprising a chemical adsorption deodorant, an olefin-based resin, and a filler; the chemical adsorption deodorant containing silicon dioxide and zinc oxide, and a content ratio between silicon dioxide and zinc oxide in the chemical adsorption deodorant is from 5:95 to 95:5 in terms of weight ratio; and wherein the olefin-based resin contains an olefin-based elastomer.

26. The stretchable film according to claim 25, wherein the olefin-based elastomer contains an α-olefin-based elastomer.

27. The stretchable film according to claim 26, wherein the α-olefin-based elastomer comprises a propylene-based elastomer.

* * * * *